US00PP32574P2

(12) United States Plant Patent
Wheeler et al.

(10) Patent No.: US PP32,574 P2
(45) Date of Patent: Dec. 8, 2020

(54) BLUEBERRY PLANT NAMED 'BB05-259MI-15'

(50) Latin Name: *Vaccinium corymbosum*
Varietal Denomination: BB05-259MI-15

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/602,946

(22) Filed: Dec. 30, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

A new and distinct cultivar of blueberry plant named 'BB05-259MI-15' as described and shown herein. 'BB05-259MI-15' is a new and distinct high chill tetraploid Northern highbush blueberry (*Vaccinium*) variety consisting of primarily *V. corymbosum*, with a limited contribution of genes from *V. ashei* and *V. darrowi*. It is a very productive late midseason maturing variety. It is characterized as having large fruit, light blue in color, and is very firm with a very small and dry picking scar. The fruit is well exposed on a vigorous medium upright bush.

5 Drawing Sheets

Latin name: *Vaccinium corymbosum.*

BACKGROUND AND SUMMARY

Blueberries are a well-known fruit enjoyed by many throughout the world. One example of an existing, patented blueberry variety is 'Bluecrop', unpatented. Another example of an existing, patented blueberry variety is 'Liberty', U.S. Plant Pat. No. 15,146.

Compared to 'Bluecrop', 'BB05-259MI-15' is more upright, the leaves are much larger in size, the date of 50% ripe fruit is 12 days later and the date of 50% open flowers is 3 days before 'Bluecrop'.

Compared to 'Liberty', 'BB05-259MI-15' is more spreading, the berry size and average weight is greater, the date of 50% ripe fruit is 5 days later, the berry firmness is greater, the date of 50% open flowers is 3 days earlier and 'BB05-259MI-15' has a rounder berry shape than 'Liberty'.

The present cultivar, 'BB05-259MI-15', provides one or more advantages compared to these and/or other blueberry varieties.

BRIEF DESCRIPTION OF THE PHOTOGRAPHS

FIG. 1 is a photograph taken in early March 2018, Grand Junction, Mich. of the Blueberry cultivar 'BB05-259MI-15', showing the color of the late winter canes and the color, the size, shape and color of the dormant buds.

FIG. 2 is a close-up photograph taken in mid-May 2018, Grand Junction, Mich. of the Blueberry cultivar 'BB05-259MI-15', showing unopened flowers, their shape and color, and the color of the peduncles and pedicels FIG. 3 is a photograph taken in early June 2018, Grand Junction, Mich. of a 6 year old bush of Blueberry cultivar 'BB05-259MI-15' showing the bush shape, abundance and color of mature leaves, the color of ripe and unripe fruit, and the relative crop load.

DETAILED DESCRIPTION

Figure 1:
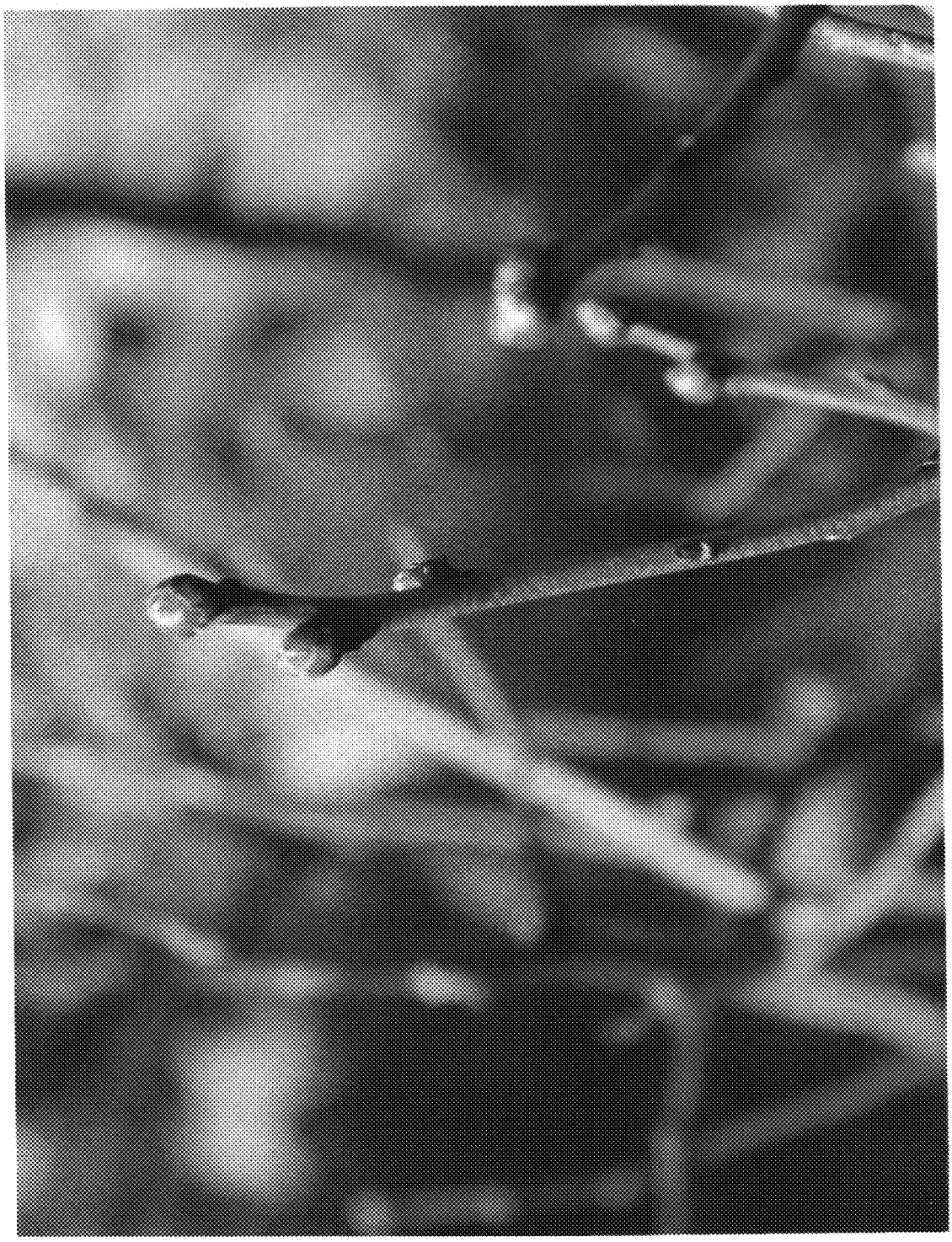
Figure 2:
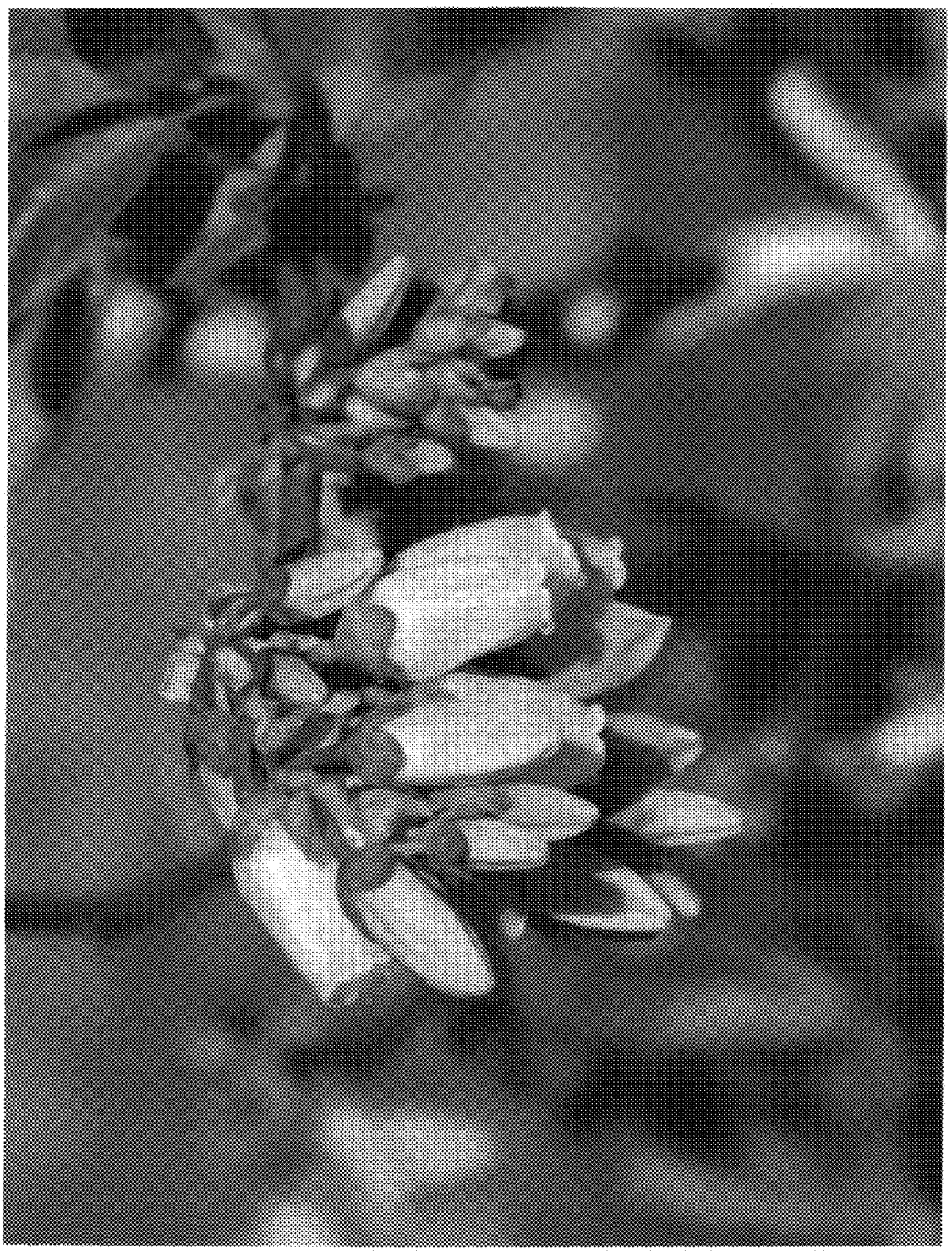
Figure 3:
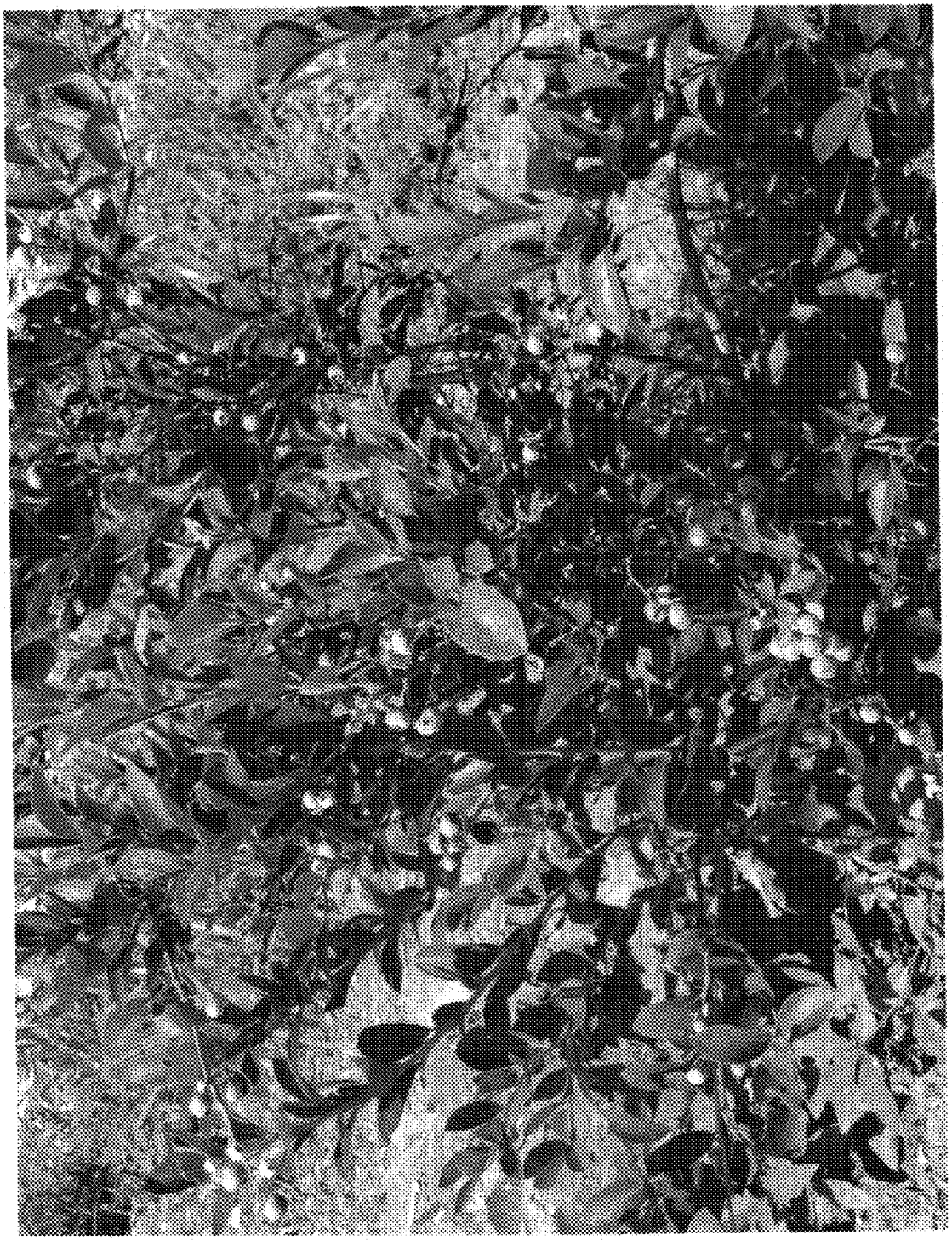
Figure 4:
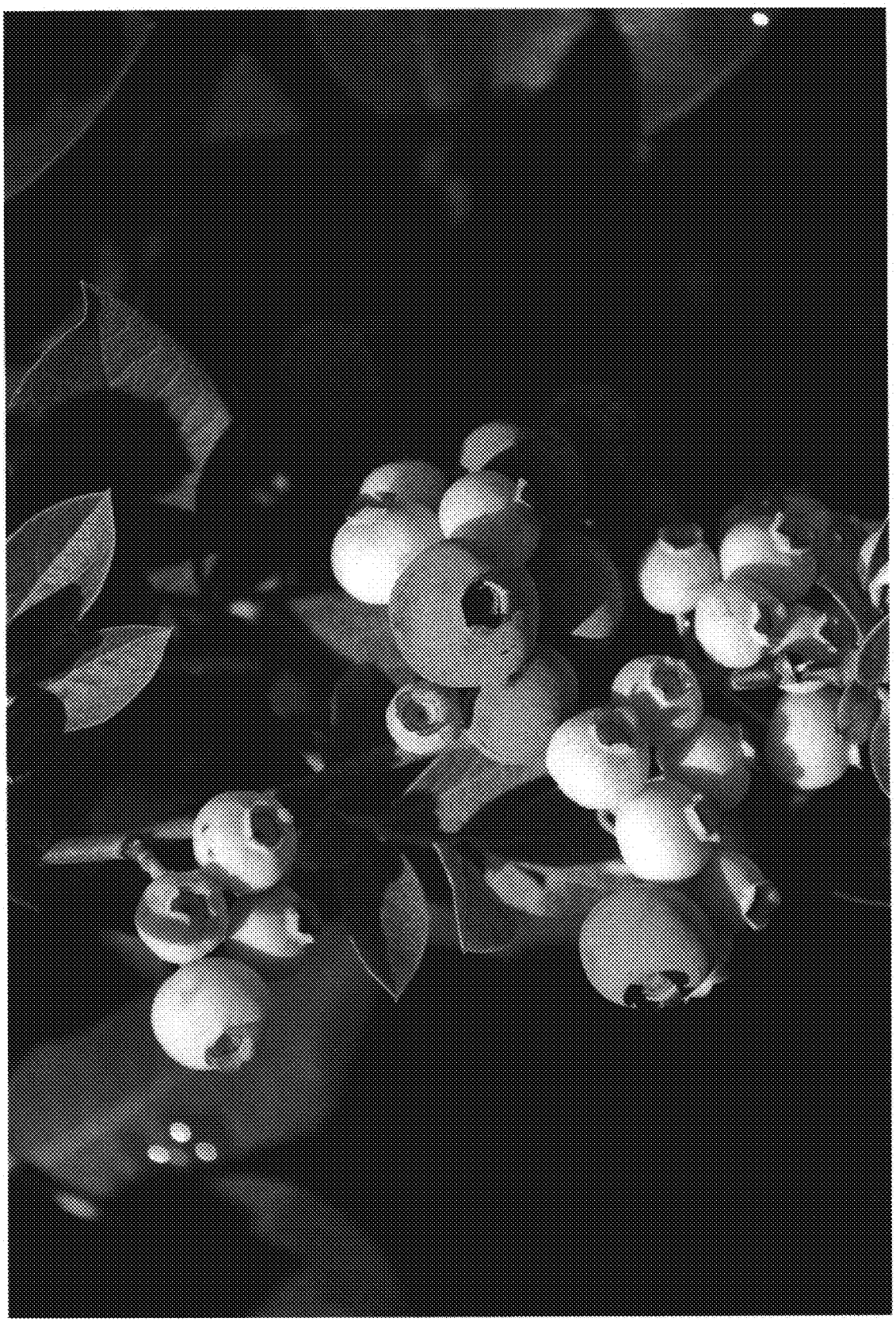
FIG. 4 is a close-up photograph taken in mid-July 2018, Grand Junction, Mich. of the Blueberry cultivar 'BB05-295MI-15' showing the ripe and unripe fruit, the shape and relative size and their color, and the shape and size of the calyx.
Figure 5:
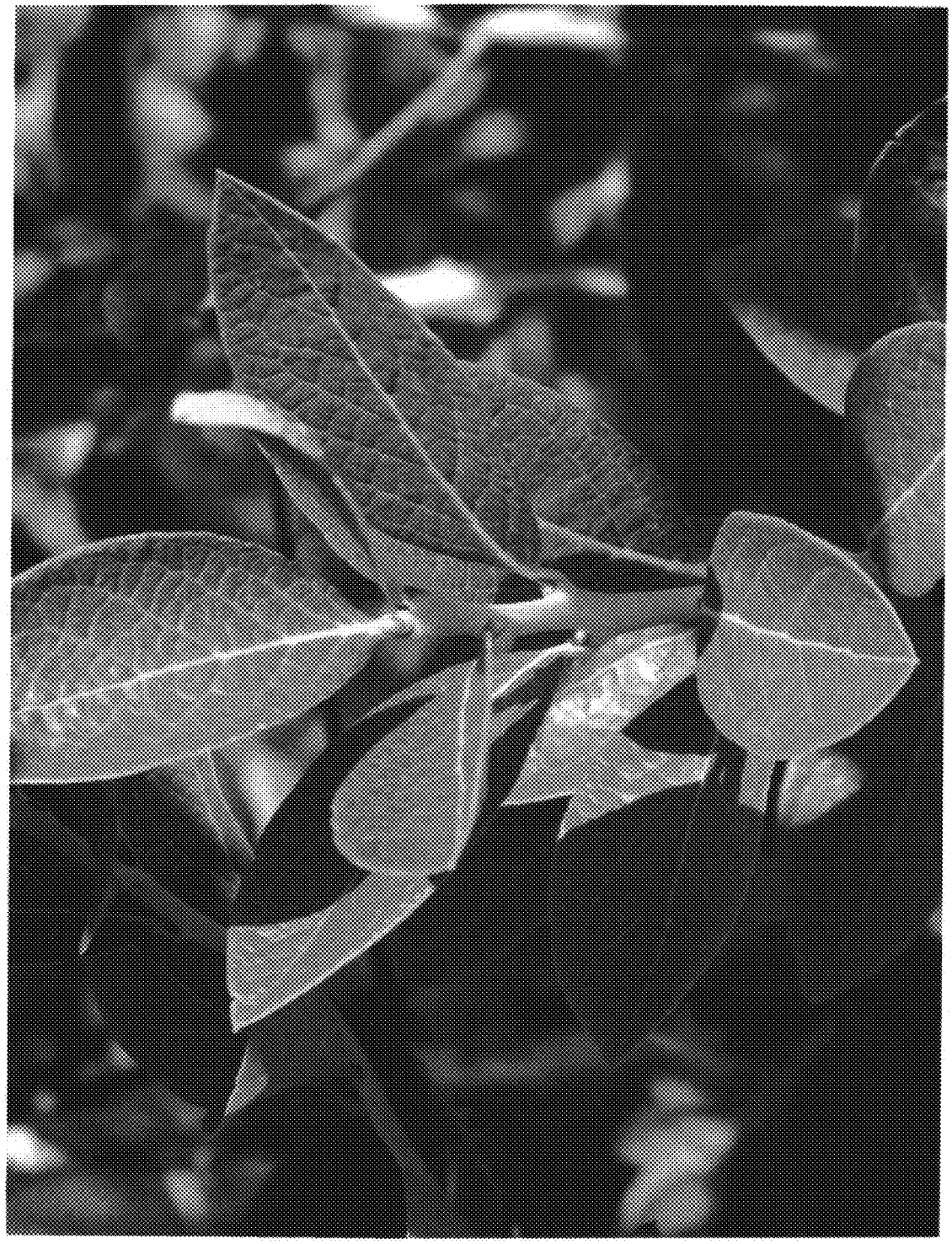
FIG. 5 is a close up photograph taken in early June 2018, Grand Junction, Mich., showing the shape, size, and color of mature leaves and their venation.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. All field observations herein were made in 2018 on 7-year-old plants located in advanced trials in Grand Junction, Mich. from plants propagated from the original selected plant. Laboratory analysis of fruit characteristics were done at Grand Junction, Mich. in 2018. All progeny have retained the characteristics of the original selection, as appropriate for the various locations cited.

Cultivar Name: 'BB05-259MI-15'.

Classification:

Family: Ericaecae.

Botanical name: *Vaccinium corymbosum.*

Common name: Blueberry.

Parentage:

FEMALE PARENT

Name: 'Brigitta'.

USPP: Unpatented.

Compared to 'Brigitta', 'BB05-259MI-15' is more upright, the weight per berry is less, the date of 50% maturity is 5 days later, the berry firmness is greater and the date of 50% open flowers is 3 days later.

MALE PARENT

'Ozarkblue'.

USPP: U.S. Plant Pat. No. 10,035.

Compared to 'Ozarkblue', 'BB05-259MI-15' has a more upright bush shape, a lighter blue colored berry, the date of 50% ripe fruit is 4 days earlier, a much firmer berry and the date of 50% flowering is 3 days earlier.

'BB05-259MI-15' originated as a seedling selected from the cross of 'Brigitta' (female) x 'Ozarkblue' (male). The seed that gave rise to 'BB05-259MI-15' was produced by hand pollination in a greenhouse in South Haven, Mich. in 2005, grown for 18 months and shipped to Muskegon, Mich. where it was planted in an observation nursery in 2007. The plant was evaluated for 3 years and first selected in 2010, based on its excellent fruit and morphological characteristics; i.e. maturity date, bush habit, berry quality, flavor, and storage ability. The bush was given the designation 'BB05-259MI-15'. 'BB05-259MI-15' was first asexually propagated by vegetative cuttings in Grand Junction, Mich. in 2010 for additional plantings in 2011. Additional plants have been propagated by softwood cuttings and tissue culture. Five and ten plants were placed in advanced trials in Grand Junction, Mich., South Haven, Mich., and Bloomington, Mich. in 2011 and 2013. All of the propagated plants have retained the original characteristics stated herein, as appropriate for the various locations cited.

'BB05-259MI-15' was first asexually propagated by vegetative cuttings for additional plantings in 2010 in Grand Junction, Mich. Micropropagation of 'BB05-259MI-15' by tissue culture was also first initiated in Middleton, Wis. in 2014. All of the propagated plants have retained the original characteristics stated herein, as appropriate for the various locations cited. This variety roots readily from hardwood or softwood cutting and as well as tissue-cultured microshoots.

All field observations were made in 2018 on plants located in advanced trials in Grand Junction, Mich. from plants propagated from the original selected plant. Laboratory analysis of fruit characteristics were done at Grand Junction, Mich. in 2018.

General comments: 'BB05-259MI-15' is a new and distinct high chill tetraploid Northern highbush blueberry (*Vaccinium*) variety consisting of primarily *V. corymbosum*, with a limited contribution of genes from *V. ashei* and *V. darrowi*. It is a very productive late midseason maturing variety. It is characterized as having large fruit, light blue in color, and is very firm with a very small and dry picking scar. The fruit is well exposed on a vigorous medium upright bush. Along with a small sized crown, a loose fruit cluster, concentrated ripening, and very firm fruit that is easily detachable, the variety displays characteristics suitable for mechanical harvest. It is intended for areas that successfully grow high chill Northern highbush varieties. Ripe fruit are large, nearly 3 grams per berry. The mean date of 50% open flowers for 'BB05-259MI-15' in Grand Junction, Mich. is May 20. Frost protection may be needed for successful pollination and fruit set. Winter chill requirement for successful flowering and leafing is at least 1000 hours below 7° C. Leaves emerge a few days before flowering commences. The mean 50% ripening date for 'BB05-259MI-15' is about July 25 in Grand Junction, Mich. The fruit shape is oblate with a medium heavy amount of waxy bloom that is rather persistent following handling. It has very good flavor, a balance of sweetness and acidity and is very juicy with a crunchy texture. It has a medium long storage capability of 3 weeks or more in refrigeration with little decline in quality.

References to color refer to The Pantone Book of Color, Eisemann and Herbert, Harry N. Abrams, Inc. Publishers, New York, ISBN 0-8109-3711-5, 1990.

Color measurements were taken with a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings: BioWorks FirmTec2, Wamena, Kans.

Average size information:

*General description.*—Medium large bush, medium upright bush shape, 5-year-old bush averages 130 cm tall, 95 cm wide, height/width ratio — 1.36.

*Growth.*—Very good growth and vigor, leafing is normal and medium abundant.

*Productivity.*—Very good.

*Cold Hardiness.*—Vegetative and flower buds −26° C., open flowers and fruit −2° C.

Specific features of the variety:

Plant:

*Growth habit.*—Medium upright.

*Plant width.*—95 cm at mid-bush.

*Plant height.*—130 cm.

*Productivity.*—8-9 pounds per bush at maturity.

*Cold hardiness/tolerance.*—Vegetative and flower buds −26° C., open flowers and fruit −2° C.

*Chilling requirement.*—1000+ hours below 7° C.

*Canes.*—Moderately branched, 5-6 canes per bush, average length of 65 cm, range 60-70 cm in length, medium number of lateral branches.

*Mature cane color.*—Pantone Smoke Gray 14-209.

*Mature cane texture.*—Rough.

*Fruiting wood.*—Immature winter color — Pantone Maroon 18-1619, immature summer color — Pantone Green Moss 17-0636.

*Internode length range.*—12-15 mm.

*Surface texture of new wood.*—Smooth.

*Mature canes.*—Circular in shape, mature width 15 mm.

*Time of beginning of leaf bud burst.*—April 26, Grand Junction, Mich.

*Time of beginning of flowering.*—May 10, Grand Junction, Mich.

*Date of* 50% *open flowers.*—May 20, Grand Junction, Mich.

*Time of* 50% *fruit ripening.*—July 25, Grand Junction, Mich.

*Disease resistance/susceptibility.*—None claimed.

*Self-Fertility.*—Highly self-fertile, pollination by another variety will enhance berry size and yield.

Foliage:

*Leaf color.*—Upper surface: Pantone Chive 19-0323, Lower surface: Pantone Grasshopper 18-0332.

*Leaf arrangement.*—Simple Alternate.

*Leaf margins.*—Entire.

*Leaf venation.*—Pinnate.

*Leaf shape.*—Elliptic.

*Leaf apices.*—Acute.
*Leaf bases.*—Acute.
*Vein and petiole coloration.*—Pantone Green Moss 17-0636.
*Petiole length.*—2 mm.
*Petiole diameter.*—1 mm.
*Petiole color.*—Pantone Green Moss 17-0636.

Leaf dimensions:
*Overall shape.*—Elliptic.
*Length.*—55-60 mm, average 57 mm.
*Width.*—20-22 mm, average 21 mm.
*Leaf margins.*—Entire.
*Nectaries.*—No nectaries visible on the leaf surface. Leaf Surface texture: Upper — smooth; Lower — smooth with slight ridging of the central and lateral veins.
*Fall leaf color.*—Pantone Holly Berry 17-1633.

Flower buds:
*Shape.*—Elliptic.
*Length.*—4 mm.
*Width.*—3 mm.
*Color.*—Pantone Crushed Berry 18-1418.

Flower:
*Flower shape.*—Elongate.
*Flower bud number.*—High.
*Flowers per cluster.*—Average 12-13 per cluster.
*Flower fragrance.*—Floral.
*Corolla color.*—Pantone Shell 13-1405.
*Corolla length.*—10 mm.
*Corolla aperture width.*—4 mm.
*Flower peduncle length.*—12 mm.
*Flower peduncle diameter.*—1 mm.
*Flower peduncle texture.*—Smooth.
*Flower peduncle color.*—Pantone Spinach Green 16-0439.
*Flower pedicel length.*—7 mm.
*Flower pedicel diameter.*—1 mm.
*Flower pedicel texture.*—Smooth
*Flower pedicel color.*—Pantone Spinach Green 16-0439.
*Calyx length* (*with sepals*).—2 mm.
*Calyx color.*—Pantone Spinach Green 16-0439.
*Stamen. Length.*—8 mm.
*Number per flower.*—10.
*Filament color.*—Pantone Cognac 18-1421.
*Style.*—Length 7 mm.
*Color.*—Pantone Cedar 16-0526.
*Pistil.*—7 mm top of ovary to stigma tip, 1 mm below the top of corolla.
*Ovary color.*—Pantone Grasshopper 18-0332.

Pollen:
*Abundance.*—Moderately abundant.
*Color.*—Pantone Buff 13-1024.

Fruit:
*Duration of ripening.*—17 days.
*Date of* 50% *maturity.*—July 25, Grand Junction, Mich.
*Berry color with wax.*—Pantone Chicory 16-4013.
*Berry color with wax removed.*—Pantone Patriot Blue 19-3925.
*Berry flesh color.*—Pantone Frozen Dew 13-0513.
*Berry surface wax abundance.*—Medium heavy, medium persistent.
*Calyx shape.*—5 point.
*Calyx diameter.*—6 mm.
*Calyx depth.*—1.5 mm.
*Berry weight.*—Average 2.7 grams/berry.
*Berry size diameter.*—17 mm.
*Observed berry shape.*—Ovate, Aspect (height/diameter): 0.76.
*Berry height.*—13 mm.
*Cluster density.*—Loose.
*Average number of fruit per cluster.*—10-12.
*Average fruit weight per cluster.*—29.7 grams.
*Detachment force.*—Easy.
*Fruit stem scar.*—Small, dry, 1 mm diameter, depth — 0.5 mm.
*Yield.*—7.3 pounds per bush.
*Berry firmness.*—Medium firm, FirmTec: 219 g/mm$^2$.
*Berry sweetness.*—Medium high, Brix° 12.7.
*Berry acidity.*—Medium high, titratable acidity — 0.43.
*Berry flavor and texture.*—Balanced flavor of sweetness and acidity, juicy and very crunchy texture.
*Self-fruitfulness.*—Highly self-fruitful.
*Storage quality.*—Excellent, storage of 3-4 weeks with little loss of quality.
*Suitability for mechanical harvesting.*—A small bush crown, a medium upright bush shape, very firm fruit and easy detachment are desirable for mechanical harvest.

Seed:
*Seed abundance in fruit.*—Medium abundant, averages 11 seed per fruit.
*Seed color.*—Pantone Burnt Orange 16-1448.
*Seed dry weight.*—NA.
*Seed size.*—1 mm length, 0.5 mm width.

Possible typical market uses: Fresh market, processing into jams, purees and yogurt.

What is claimed is:

1. A new and distinct cultivar of Blueberry plant named 'BB05-259MI-15' as described and shown herein.

* * * * *